(12) United States Patent
Biedermann et al.

(10) Patent No.: US 6,168,597 B1
(45) Date of Patent: Jan. 2, 2001

(54) BONE SCREW

(76) Inventors: Lutz Biedermann, Am Schäfersteig 8, D-78048 VS-Villingen; Jürgen Harms, Vogesenstr. 60, D-76337 Waldbronn, both of (DE)

(*) Notice: Under 35 U.S.C. 154(b), the term of this patent shall be extended for 0 days.

(21) Appl. No.: 08/930,149

(22) PCT Filed: Feb. 7, 1997

(86) PCT No.: PCT/EP97/00567

§ 371 Date: Oct. 8, 1997

§ 102(e) Date: Oct. 8, 1997

(87) PCT Pub. No.: WO97/31574

PCT Pub. Date: Sep. 4, 1997

(30) Foreign Application Priority Data

Feb. 28, 1996 (DE) .............................. 196 07 517

(51) Int. Cl.⁷ ............................................. A61B 17/56
(52) U.S. Cl. ............................................................. 606/73
(58) Field of Search .................................. 606/73, 72, 61, 606/60, 104

(56) References Cited

U.S. PATENT DOCUMENTS

| | | | |
|---|---|---|---|
| 4,611,581 | * | 9/1986 | Steffee .................................... 606/73 |
| 4,716,893 | * | 1/1988 | Fischer et al. ........................ 606/73 |
| 4,760,843 | * | 8/1988 | Fischer et al. ........................ 606/73 |
| 5,489,210 | * | 2/1996 | Hanosh ................................. 606/73 |

FOREIGN PATENT DOCUMENTS

| | | | |
|---|---|---|---|
| 39 36 703 A1 | | 5/1991 | (DE) . |
| 39 36703 A1 | * | 5/1991 | (DE) ..................................... 606/73 |
| 39 36 703 C2 | | 9/1992 | (DE) . |
| 0 504 915 A1 | * | 9/1992 | (EP) ..................................... 606/73 |
| 209 422 | | 8/1992 | (HU) . |
| WO/91 11967 | | 8/1991 | (WO) . |

\* cited by examiner

*Primary Examiner*—Michael Buiz
*Assistant Examiner*—(Jackie)Tan-Uyen Thi Ho
(74) *Attorney, Agent, or Firm*—George W. Neuner; Dike, Bronstein, Roberts and Cushman, LLP

(57) ABSTRACT

A bone screw (1) having a threaded shaft portion (2) and a head (3) is provided. In order to ensure a good fastening capability of the bone screw even in soft bone material the bone screw has a longitudinal bore (5) extending along the longitudinal axis of the threaded shaft portion (2) and having a portion (7) which flares towards the free end (6) opposite to the head (3). Slits (8) extending parallel to the longitudinal axis are provided in this portion of the threaded shaft portion. An expanding member (20) comprises a top portion (22) forming the top (22) of the bone screw (1) and a shaft (21) adjacent thereto extending into the longitudinal bore (5). The threaded shaft portion is provided with notches at its inner wall adjacent to the flared portion (7) of the longitudinal bore (5), the notches surrounding the longitudinal bore (5) in a defined region thereof. When expanding the bone screw within the bone, the top portion (22) is pulled into the longitudinal bore (5) in such a manner that a peripheral edge (25) at the top portion (22) engages the notches (9) of the threaded shaft portion (2). This expands the end of the bone screw (1) screwed into the bone.

9 Claims, 1 Drawing Sheet

BONE SCREW

The invention relates to a bone screw according to the preamble of claim 1.

Such a bone screw is known from DE 39 36 703 C2. The free front end of the threaded shaft of this bone screw is expanded by means of an expanding member introduced into a longitudinal bore of the screw. This expansion serves, on the one hand, as a safety device against reversed rotation and, on the other hand, to increase the anchoring forces acting between the bone material and the screw thread.

The necessary screwing mechanism requires a minimum dimension.

It is the object of the invention to provide a bone screw with an exceptionally small diameter and a lock against reverse rotation, which bone screw is capable to be anchored in the bone and can, after being screwed into the bone, be expanded at its top portion in a finely controlled manner in a second operating step.

This object is achieved by a bone screw according to claim 1.

Further developments of the invention are defined in the subclaims.

Embodiments of the invention will be described below with reference to the Figures.

In the Figures:

FIG. 3 is a partially sectional representation of the bone screw in an assembled state before screwing it in;

Figure 2:
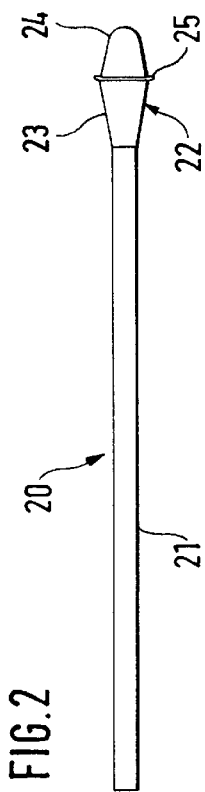
FIG. 2 shows the expanding member of the bone screw.

As shown in the FIGS. 1 to 4 the bone screw 1 has a threaded shaft portion 2 and a head 3 unitarily formed therewith. The threaded shaft portion 2 has an external thread 4 as conventionally used for bone screws. As in particular shown in FIG. 1, a coaxially aligned longitudinal bore 5 extends through the interior of the bone screw 1.

The bone screw has a coaxial conical recessed portion 7 formed at the free end 6 of the bone screw opposite to its head 3, the recessed portion 7 flaring towards the free end 6. Slits 8 are formed in the wall of the threaded shaft portion 2 and extend from the free end 6 opposite to the head 3 parallel to the longitudinal axis of the threaded shaft portion 2. The slits 8 have a length which slightly exceeds half of the length of the threaded shaft portion 2. However, the length of the slits is at least twice the axial length of the conical recessed portion 7. Preferably a pair of such slits is provided, the slits being angularly offset by 180° with respect to each other.

In a portion of the longitudinal bore 5 adjacent to the conical recessed portion 7 the surface has a substantially sawtooth-shaped portion 9. The sawtooth-shaped portion 9 is formed by peripheral notches in the inner wall of the threaded shaft portion, whereby the teeth formed by the notches each have a flank facing the head 3 and a flank facing the free end 6. The flank facing the head 3 is, in an unexpanded state of the threaded shaft portion 2, aligned substantially perpendicular to the longitudinal axis of the threaded shaft portion, whereas the flank of the teeth facing the free end 6 includes an acute angle with the longitudinal axis. The sawtooth-shaped portion 9 extends over an axial length of the screw which is at least equal to the axial length of the conical recessed portion 7.

The head 3 comprises a recess 10 formed in axial direction at the side opposite to the free end 6. The recess 10 is formed to allow the bone screw 1 to be screwed into a bone using this recess and a screw driver cooperating therewith. For example, the recess 10 has a hexagon shape for engagement with a hexagon screw driver.

An expanding member 20 serving as tie rod consists of a rod-shaped shaft 21 with a top portion 22 formed at the end thereof. The diameter of the shaft 21 is sized so that the shaft 21 is guided within the longitudinal bore 5 of the bone screw, but displaceable therein in axial direction. The length of the shaft 21 is greater than the length of the bone screw 1 in axial direction by such an amount that the shaft 21 when inserted into the screw projects from the head 3 and exhibits sufficient working surface for engagement with a tool cooperating therewith. The top portion 22 has, on its side adjacent to the shaft 21, an outer wall having a conical portion 23 tapering towards the shaft 21 and designed to positively fit into the conical recessed portion 7. On its side facing away from the shaft 21 and, thus, from the head 3 of the bone screw 1 the top portion 22 has a point 24 forming the top end of the bone screw. The point 24 is likewise conical, tapering towards the side facing away from the head 3. The free end of the point 24 is rounded. About at its axial center the top portion 22 has a peripheral edge 25 with a diameter which is slightly greater than the diameter of the conical recessed portion 7 at the free end 6. The edge 25 is formed by the fact that the portion of the point 24 immediately adjacent to the conical portion 23 of the top portion 22 has a smaller diameter than the conical portion 23 which therefore forms a shoulder. The edge 25 is sized to be capable to catch the teeth of the sawtooth-shaped portion 9 when the expanding member is placed into the threaded shaft part and pulled in direction towards the head.

A suitable screw driver for screwing in the bone screw comprises a central longitudinal bore for receiving the shaft 21 of the expanding member 20.

Figure 4:
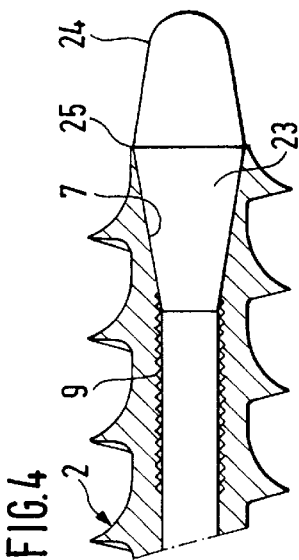
FIG. 4 is an enlarged, partially sectional representation of the top portion of the bone screw of FIG. 3.
Figure 3:
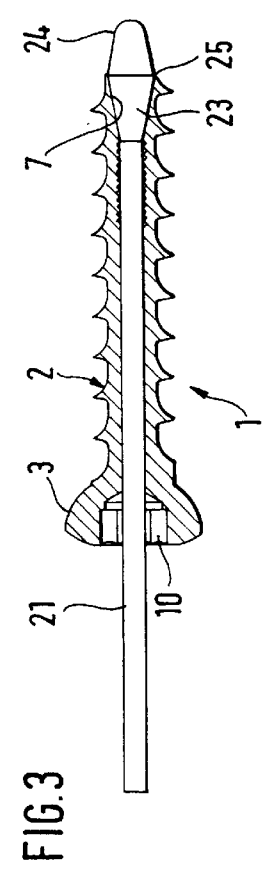

In operation the shaft 21 is first pushed into the longitudinal bore 5 starting from the free end 6 of the threaded shaft portion until the conical portion 23 of the top portion 22 rests within the conical recessed portion 7 and the bone screw has the usual point 24, as shown in the FIGS. 3 and 4. The end of the shaft 21 opposite to the point 24 projects from the head 3 of the screw. The screw is now screwed in in conventional manner using the screw driver.

Figure 6:
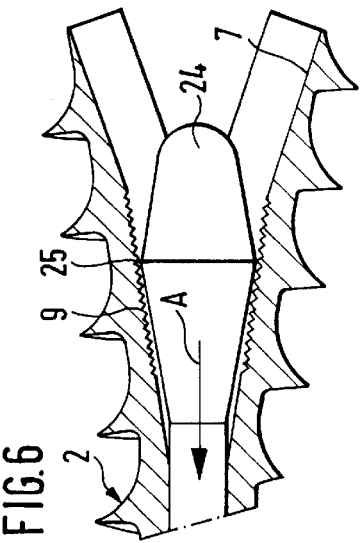
FIG. 6 is an enlarged representation of the expanded front end of the bone screw of FIG. 5.
Figure 1:
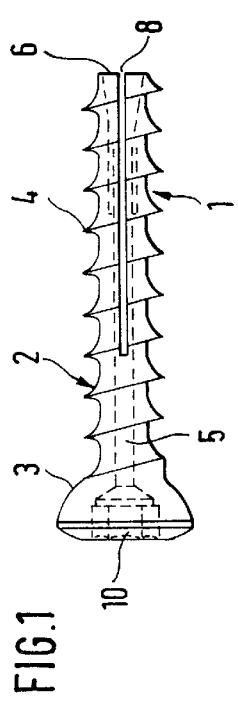
FIG. 1 shows the threaded shaft part and the head of the bone screw.
Figure 5:
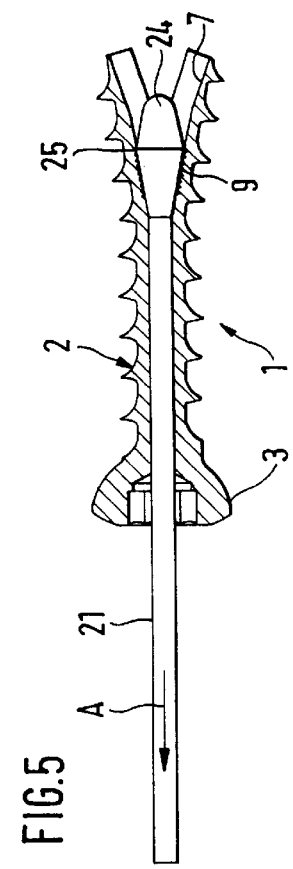
FIG. 5 is a partially sectional representation of the bone screw with expanded front end in a screwed-in state.

As shown in particular in FIGS. 5 and 6, the free end of the threaded shaft portion 2 is, after the bone screw 1 has been precisely positioned, expanded by exerting tensile forces on the shaft 21 of the expanding member 20 in direction of the arrow A in FIG. 5. The tensile forces are exerted onto the shaft 21 by engaging the free part of the shaft 21 with a type of rivet setter which is supported at the screw head 3. This pulls the top portion 22 into the longitudinal bore 5 of the threaded shaft portion 2 so that the edge 25 is locked in the teeth of the portion 9. The slotted portion is thereby expanded in a finely controlled manner. After the expanding operation is finished, the projecting part of the shaft 21 is cut off.

It is not necessary that the portion 9 is sawtooth-shaped. The notches may also be formed with a curved surface of the teeth. However, it is essential that the slope of the flanks is such that the top portion 22 can not be released by itself from the notches in the expanded state.

I claim:

1. A bone screw comprising:

a screw head, a threaded shaft portion having a longitudinal axis and a free end opposite to said screw head, a longitudinal bore extending along said longitudinal axis through said threaded shaft portion, said longitudinal bore comprising a flared portion at said free end, at least two slits formed in said threaded shaft portion in the region of said flared top portion, said slits extending parallel said longitudinal axis, an expanding member comprising a to portion forming a top of said bone screw and a shaft extending through said longitudinal bore, and locking means provided at said top portion and at said threaded shaft portion for locking said top portion in said threaded shaft portion.

2. The bone screw of claim 1, wherein said locking means comprises notches formed at an inner wall of said threaded shaft portion and a projection formed at said top portion for engaging said notches.

3. The bone screw of claim 1, wherein said expanding member is formed of a single piece, said top portion being provided at an end of said shaft.

4. The bone screw of claim 1, wherein said flared portion is substantially conical.

5. A bone screw comprising:

a screw head, a threaded shaft portion having a longitudinal axis and a free end opposite to said screw head, a longitudinal bore extending along said longitudinal axis through said threaded shaft portion, said longitudinal bore comprising a flared portion at said free end, at least two slits formed in said threaded shaft portion in the region of said flared portion, said slits extending parallel to said longitudinal axis, an expanding member comprising a top portion forming a top of said bone screw and a shaft extending through said longitudinal bore, and locking means provided at said top portion and at said threaded shaft portion for locking said top portion in said threaded shaft portion, where said top portion comprises a first, substantially conical portion which tapers towards said shaft, and a second portion adjacent to said first portion, said second portion tapering towards said top of said bone screw, said substantially conical first portion positively fitting into said flared portion.

6. The bone screw of claim 2, wherein said notches are formed at an inner wall of said threaded shaft portion adjacent to said flared portion, and wherein said projection for engaging said notches is formed as a radial projection at a place of maximum diameter, measured perpendicular to said longitudinal axis, of said top portion.

7. The bone screw of claim 2, wherein said projection is formed by a radially projecting edge provided in peripheral direction of said top portion.

8. The bone screw of claim 2, wherein said notches comprise a sawtooth-shaped portion.

9. A bone screw comprising:

a screw head, a threaded portion having a longitudinal axis and a free end opposite to said screw head, a longitudinal bore extending along said longitudinal axis through said threaded shaft portion, said longitudinal bore comprising an internal flared portion at said free end, at least two slits formed in said threaded shaft portion in the region of said flared portion, said slits extending parallel to said longitudinal axis, an expanding member comprising extending a top portion forming a top of said bone screw and a shaft extending through said longitudinal bore, and locking means provided at said top portion and at said threaded shaft portion for locking said top portion in said threaded shaft portion.

\* \* \* \* \*